(12) United States Patent
Hettrick et al.

(10) Patent No.: US 7,336,994 B2
(45) Date of Patent: Feb. 26, 2008

(54) CONTROL OF ATRIAL DEFIBRILLATION THERAPY BASED ON HEMODYNAMIC SENSOR FEEDBACK

(75) Inventors: Douglas A. Hettrick, Blaine, MN (US); David E. Euler, Maple Grove, MN (US); Eduardo N. Warman, Maple Grove, MN (US); Michael R. Ujhelyi, Maple Grove, MN (US); Rahul Mehra, Stillwater, MN (US); Paul D. Ziegler, Minneapolis, MN (US); Shailesh Kumar V. Musley, Blaine, MN (US); Charles E. Distad, St. Paul, MN (US); David E. Ritscher, Minneapolis, MN (US)

(73) Assignee: Medtronic, Inc., Minneapolis, MN (US)

( * ) Notice: Subject to any disclaimer, the term of this patent is extended or adjusted under 35 U.S.C. 154(b) by 240 days.

(21) Appl. No.: 10/760,155

(22) Filed: Jan. 16, 2004

(65) Prior Publication Data

US 2005/0159783 A1    Jul. 21, 2005

(51) Int. Cl.
*A61N 1/39* (2006.01)

(52) U.S. Cl. .................. 607/5; 607/4; 607/6; 607/7

(58) Field of Classification Search .................. 607/3, 607/4–7, 9, 17, 18, 22, 23, 25
See application file for complete search history.

(56) References Cited

U.S. PATENT DOCUMENTS

| 4,984,572 A | 1/1991 | Cohen .................. 128/419 D |
| 5,156,148 A * | 10/1992 | Cohen .................. 607/4 |
| 6,317,626 B1 | 11/2001 | Warman .................. 600/523 |
| 6,522,914 B1 | 2/2003 | Huvelle et al. .................. 600/509 |
| 2002/0120300 A1* | 8/2002 | Thong et al. .................. 607/5 |
| 2003/0014083 A1 | 1/2003 | Kupper .................. 607/9 |
| 2003/0144701 A1 | 7/2003 | Mehra et al. .................. 607/17 |

FOREIGN PATENT DOCUMENTS

WO    WO 03/020364 A2    3/2003

* cited by examiner

*Primary Examiner*—Robert Pezzuto
*Assistant Examiner*—Shevon Johnson
(74) *Attorney, Agent, or Firm*—Daniel G. Chapik (57) ABSTRACT

Control of defibrillation therapy delivered by implantable medical devices (IMDs) using hemodynamic sensor feedback is disclosed. The hemodynamic sensor feedback allows for increased control over application of atrial defibrillation therapy. Specifically, the therapy is delivered when a fibrillation episode results in a discrete loss of hemodynamic function. Defibrillation therapy is thus withheld for hemodynamically benign arrhythmias.

37 Claims, 5 Drawing Sheets

CONTROL OF ATRIAL DEFIBRILLATION THERAPY BASED ON HEMODYNAMIC SENSOR FEEDBACK

TECHNICAL FIELD

The invention relates to cardiac defibrillation systems, and more particularly to atrial defibrillation systems.

BACKGROUND

Patients who have experienced atrial or ventricular fibrillation or who meet a risk profile for atrial or ventricular fibrillation can receive an implantable defibrillator. When an implantable defibrillator identifies the presence of an atrial and/or ventricular fibrillation, the device delivers one or more high energy electrical pulses to the patient to stop the fibrillation and allow the heart to reestablish a normal sinus rhythm.

Ventricular fibrillation is life threatening and requires immediate delivery of defibrillation to terminate the fibrillation. Delivery of high energy atrial defibrillation is also effective to terminate atrial fibrillation; however, atrial defibrillation s often not life threatening. Thus, immediate delivery is not always required. Even so, atrial fibrillation often affects the quality of life of the patient due to the reduced hemodynamic performance of the heart. For those patients having frequent or chronic atrial fibrillation, high defibrillation frequency and the associated discomfort and anxiety is a major deterrent to therapy acceptance.

SUMMARY

In one embodiment of the present invention, application of defibrillation therapy delivered by implantable medical devices (IMDs) is controlled using hemodynamic sensor feedback. Thus, application of high energy atrial defibrillation is reduced or minimized and shock benefit is increased or maximized by prioritizing shock delivery to atrial arrhythmias associated with hemodynamic compromise. The embodiment provides increased control over application of high energy atrial defibrillation therapy. Specifically, such therapy is delivered only when the arrhythmia results directly in a discrete loss of hemodynamic function. In one embodiment, defibrillation is not delivered to hemodynamically benign arrhythmias thus reducing the total number of defibrillation episodes that are delivered in an individual patient. At the same time, the therapy that is delivered has a higher probability of providing patient benefit.

In one embodiment, the invention is directed to a method in which fibrillation is detected, the hemodynamic performance of the heart is measured, and therapy is enabled based on the measured hemodynamic performance.

In another embodiment, the invention is directed to a system for controlling application of therapy to a heart, wherein the system includes a first sensor that detects fibrillation, a second sensor that measures hemodynamic performance of the heart, and a processor that determines whether hemodynamic compromise is present based on the measured hemodynamic performance, and enables therapy to alleviate effects of the fibrillation when hemodynamic compromise is present.

In another embodiment, the invention is directed to a computer-readable medium containing instructions. The instructions cause a programmable processor to detect fibrillation, measure hemodynamic performance during fibrillation, determine presence of hemodynamic compromise based on the measured hemodynamic performance, and enable therapy when hemodynamic compromise is present.

The details of one or more embodiments of the invention are set forth in the accompanying drawings and the description below. Other features, objects, and advantages of the invention will be apparent from the description and drawings, and from the claims.

DETAILED DESCRIPTION

In general, the invention controls application of therapy to a heart based on hemodynamic sensor feedback. One embodiment controls application of atrial defibrillation therapy delivered by an implantable medical device (IMD) using hemodynamic sensor feedback.

Ventricular fibrillation is a life threatening condition requiring immediate delivery of therapy to restore normal sinus rhythm. Atrial fibrillation is not necessarily life threatening but may result in a decrease in hemodynamic performance of the heart and thus a reduced quality of life for a patient. Although application of atrial defibrillation therapy can often terminate atrial arrhythmias, frequent application of electrical stimulation in the form of atrial defibrillation therapy may be perceived as undesirable to certain patients. For example, delivery of high energy therapy to the heart is a very uncomfortable experience for most patients. Furthermore, some atrial fibrillation episodes and their resultant consequences are not perceived by the patient as negatively affecting their quality of life. The use of high energy atrial defibrillation may be counter-productive to patient acceptance because the perceived benefit of the therapy may be outweighed by the severity and discomfort of the therapy. The discomfort and anxiety associated with defibrillation is a major concern for some patients. Furthermore, delivery of therapy in such cases causes unnecessary drain on the IMD's battery, reducing device longevity.

There are instances when atrial fibrillation results in hemodynamic compromise substantial enough to adversely affect the patient's quality of life. For example, restoration of sinus atrial rhythm may be particularly important in patients with ventricular dysfunction. In these cases, the reduction in ventricular filling and atrial transport function associated with atrial fibrillation may exacerbate existing ventricular dysfunction and lead to hemodynamic decompensation, such as pulmonary vascular congestion, increased atrial volume, atrial pressure and pulmonary venous flow, pulmonary venous dimension as well as decreased blood pressure (arterial or ventricular), ventricular contractility, cardiac output, stroke volume resulting in increased ventricular end-systolic or end diastolic dimension and decreased ejection fraction, ejection time, myocardial acceleration, and mitral valve flow.

Accordingly, embodiments of the present invention provide increased control over the application of high energy atrial defibrillation therapy. For example, therapy is delivered when a detected episode of atrial arrhythmia results directly in a discrete loss of hemodynamic function. Therapy is not applied to hemodynamically benign arrhythmias and thus fewer total defibrillations may be delivered in an individual patient. At the same time, the therapy that is delivered has an increased probability of providing patient benefit. Defibrillation therapy is thus associated with greater actual and/or perceived increases in hemodynamic function. All of these factors combine to result in greater therapy acceptance by a patient.

Although the present invention will be described primarily with reference to high energy atrial defibrillation therapy, the invention is not so limited. For example, the same techniques can be used to control the operation of other device-based therapies such as low energy anti-tachycardia pacing or pacing prevention algorithms. The same techniques can also be used to hemodynamically optimize other implantable device features including lower rate, AV delay and mode switching. For example, the device could automatically adjust the paced or sensed AV delay in order to minimize left atrial size, or to maximize contractility. The same techniques can also be used to control the operation of other types of therapy delivery systems such as drug delivery systems.

Figure 1:
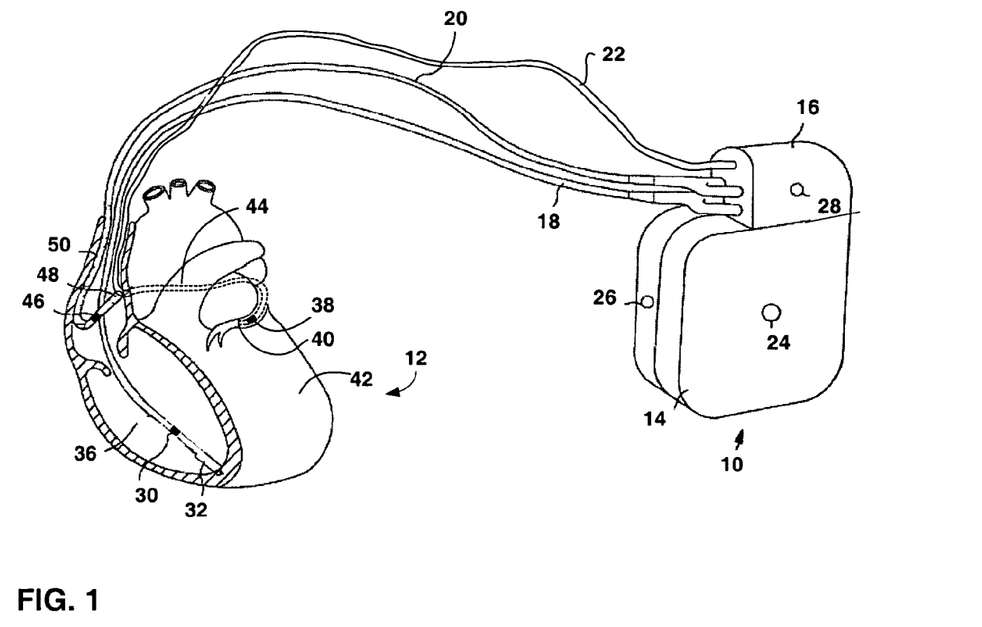
FIG. 1 is a conceptual diagram illustrating an example implantable medical device (IMD).

FIG. 1 is a diagram illustrating an implantable medical device (IMD) 10 in association with a heart 12. IMD 10 may be configured for both monitoring and therapy of heart 12. For example, IMD 10 may include a pulse generator to deliver electrical stimulation to heart 12 for use in pacing and/or appropriate capacitive capability for cardioversion or defibrillation.

IMD 10 is generally configured to permit subcutaneous implantation within a human body, e.g., within upper thoracic regions or the lower abdominal region. IMD 10 includes a hermetically sealed housing 14 having a connector block assembly 16 that receives the proximal ends of one or more cardiac leads for connection to circuitry within the housing. In the example of FIG. 1, connector block assembly 16 receives three cardiac leads. In particular, connector block assembly receives a right ventricular (RV) endocardial lead 18, a left ventricular (LV) epicardial lead 22, and a right atrial (RA) endocardial lead 20. In other embodiments, IMD 10 may include more or fewer leads. In some embodiments, housing 14 functions as an electrode, along with a set of electrodes 24, 26, 28 provided at various locations on the housing or connector block assembly 16. The different leads may include electrodes for pacing and/or high voltage electrodes 36, 50 and 44, respectively, for delivery of cardioversion or defibrillation shocks.

In general, each lead 18, 20 and 22 includes pace/sense electrodes 30, 46 and 38, respectively, which IMD 10 uses to sense electrical signals attendant to the depolarization and repolarization of heart 12 and thus detect arrhythmias such as fibrillation. In some embodiments, IMD 10 uses these electrodes on leads 18, 20, and 22 to provide pacing pulses to heart 12, although the techniques described herein are not limited in that respect. For example, electrodes used for sensing and pacing can be unipolar or bipolar, as is well known in the art.

IMD 10 is capable of defibrillation or cardioversion therapy, via electrodes 36, 50 and 44 located on leads 18, 20 and 22, respectively. For example, IMD 10 detects ventricular fibrillation of heart 12, and delivers defibrillation therapy to heart 12 in the form of electrical stimulation. In that case, one or more high voltage capacitors within IMD 10 are rapidly charged to a desired energy level, and then discharged to deliver the defibrillation energy to heart 12. By way of example, defibrillation electrode 30 disposed on LV lead 18 may be used to deliver such shocks. Housing 16 of IMD 10 functions as the ground electrode when shocks are delivered to defibrillation electrode 30.

IMD 10 can also deliver atrial defibrillation therapy to heart 12 in the form of electrical shocks. For example, defibrillation electrode 50 disposed on lead 20 can be used to deliver such therapy. Housing 16 of IMD 10 again functions as the ground electrode when shocks are delivered to defibrillation electrode 30.

In various embodiments, atrial defibrillation is selectively delivered. For example, atrial defibrillation is delivered when a threshold change in hemodynamic performance of the heart is detected. Thus, even if an atrial arrhythmia such as fibrillation is present, therapy is withheld unless a threshold change in hemodynamic performance is met.

In another embodiment, criteria used to determine therapy delivery includes a time of day component (e.g., night) or some other preprogrammed time component. If the hemodynamic performance does not meet at least a threshold change relevant to the applicable time period, the programmed therapy is withheld.

Figure 2:
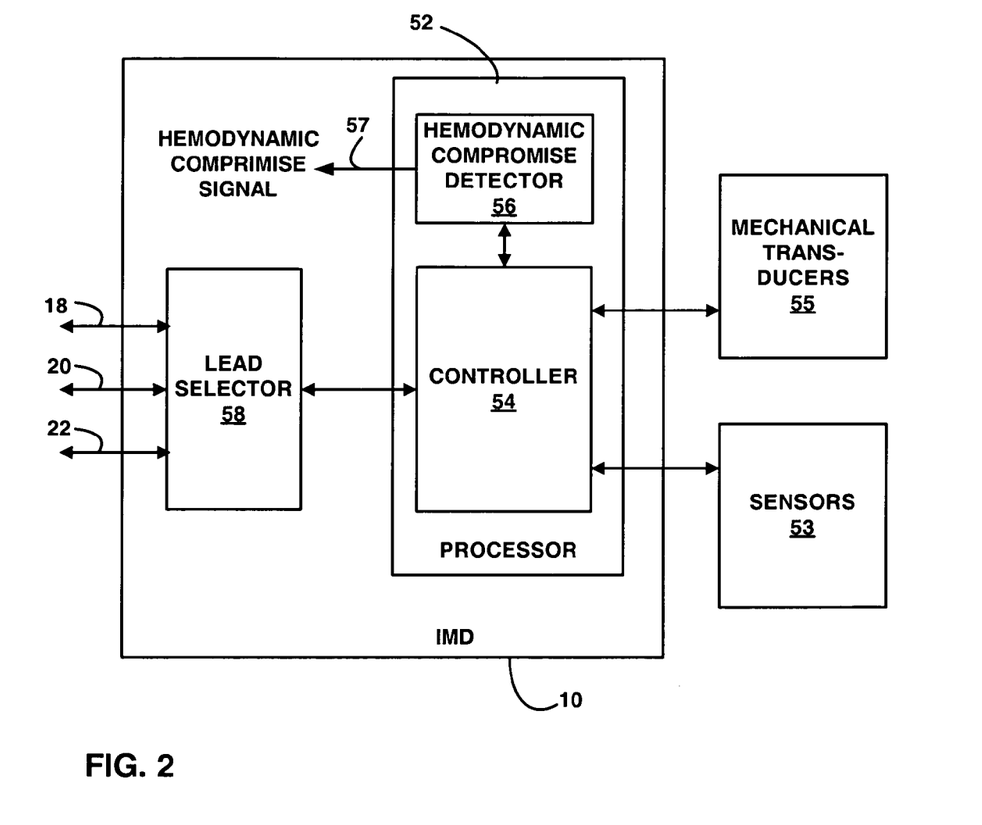
FIG. 2 is a functional block diagram of the IMD shown in FIG. 1.

FIG. 2 is a block diagram illustrating an embodiment of an IMD 10 configured for detection of hemodynamic compromise in a patient. Device 10 includes a lead selector circuit 54 that selects one or more of the leads 18, 20 and 22 and a processor 52. Processor 52 may be realized by a microprocessor, digital signal processor, ASIC, FPGA, or other integrated or discrete logic circuitry programmed or otherwise configured to provide functionality as described herein.

Processor 52 provides, for example, a controller 54 and a hemodynamic compromise detector 56. Controller 54 and hemodynamic compromise detector 56 may be programmable features or functional blocks of processor 52. Controller 54 controls the operation of lead selector 58. The electrical signals representative of the cardiac cycle obtained via the leads 18, 20 and 22 can be used to identify arrhythmia or other abnormalities. The signals obtained via the leads 18, 20 and 22 can also be used to measure the relevant hemodynamic performance parameters.

In other embodiments, controller 56 may receive signals from one or more mechanical transducers 55, such as a pressure signal from a pressure transducer or a signal indicative of the physical activity level of a patient from an activity level monitor, such as an accelerometer. The mechanical transducers can also be used to measure corresponding hemodynamic performance parameters. Other sensors 53 external to the IMD 10 may also be provided to supply the desired hemodynamic performance information.

Many different hemodynamic performance parameters could be used to measure the hemodynamic performance. These hemodynamic performance parameters can include, but are not limited to, electrogram (EGM), electrocardiogram (ECG), pressure (atrial, ventricular, arterial, venous) flow, pulmonary venous flow, acceleration, atrial or ventricular dimension/volume, thoracic or intramyocardial impedance, velocity, QT interval, ST segment, blood oxygen content, myocardial oxygen consumption, change in right ventricular pressure versus time (dRVP/dt), MVO2/PO2 and/or other hemodynamic performance parameters. Each of these hemodynamic performance parameters is ascertained from the appropriate signals sensed by leads 18, 20 and 22, by mechanical transducers 55 contained either within IMD 10 or external to IMD 10, other implanted sensors in connectivity with IMD 10, other sensors 53 or by other methods well known to those of skill in the art.

A number of sense amplifiers (not shown) amplify the signals received from leads 18, 20, 22, from mechanical transducers 55, or from other sensors 53 and provide the amplified signals to controller 54. Controller 54 can include sampling and comparator circuitry for analysis of the electrical signals relative to criteria such as average, peak-to-peak, or total amplitude thresholds. Alternatively, processor 52 may digitally sample the amplified signals and perform a software-based analysis of the digital signals. Thus, controller 54 may include an analog-to-digital converter that converts the analog signals produced by lead selector circuit 58 and/or mechanical transducers into digital samples for analysis by processor 52.

The signals are then sent to hemodynamic compromise detector 56, which may be a programmable feature or module within processor 52. Hemodynamic compromise detector 56 processes the relevant information to determine whether hemodynamic compromise is present.

Hemodynamic compromise can be detected when a change in hemodynamic performance exceeds a threshold. In one embodiment, hemodynamic compromise is detected when the hemodynamic performance during fibrillation differs from the hemodynamic performance measured during normal sinus rhythm by more than a threshold value. The threshold value may be a nominal value derived from a typical implanted cardioverter-defibrillator device (ICD) population of patients. Alternatively, the threshold value may be independently adjusted and set for a given patient as desired by the attending physician. In addition, the threshold value may be expressed as an absolute change, a percentage change, or an integrated change over a period of time of the relevant hemodynamic performance parameter or parameters.

For analysis purposes, the hemodynamic performance data as determined by the processor and the hemodynamic compromise detector, with a time and date stamp, as well as other information, may be stored in a memory associated with IMD 10, along with data regarding the type of arrhythmia to facilitate diagnosis by the attending physician.

In operation, in one embodiment, processor 52 determines the hemodynamic performance of the heart during normal sinus rhythm (NSR) to obtain an NSR index. The NSR index provides a baseline for the particular patient against which hemodynamic performance during an atrial arrhythmia is compared. Similarly, when atrial tachycardia (AT) or atrial fibrillation (AF) is detected, processor 52 determines the hemodynamic performance of the heart during AT or AF to obtain an AT/AF index. In one embodiment, the NSR index and the AT/AF index could be one-time measurements, or could be a series of samples obtained as a function of time. In another embodiment, the NSR and/or AT/AF indices could be updated over time. For example, the NSR and/or AT/AF indices could represent a mean or median hemodynamic performance index over a period of n preceding samples.

Hemodynamic compromise detector 56 compares the AT/AF index to the NSR index to identify a change in hemodynamic performance. When the change in hemodynamic performance exceeds a predetermined threshold, hemodynamic compromise detector 56 indicates a hemodynamic compromise condition within heart 12 and generates a hemodynamic compromise signal 57. The hemodynamic compromise signal 57 may be used to enable and/or drive selection and delivery of one or more therapies as described below with respect to FIG. 4. Conversely, in some embodiments, the absence of the hemodynamic compromise signal 57 may be used to inhibit selection and delivery of one or more therapies.

For example, in one embodiment, the monitored hemodynamic parameter is mean arterial blood pressure, the programmed threshold is expressed as an absolute change (10 mmHg, for example), and the minimum duration is 60 minutes after onset of atrial fibrillation. If the patient's mean arterial blood pressure drops from 100 mmHg to 85 mmHg and remains at that level for at least 60 minutes, then defibrillation therapy would be enabled. This is because the change in pressure (100−85=15 mmHg) is greater than the threshold value (10 mmHg) for the required minimum time period. Conversely, if the pressure were to drop to only 95 mmHg, therapy would be withheld, since the threshold has not been met and thus existence of at least a minimum amount of hemodynamic compromise has not been detected. In this example embodiment, therapy would also be withheld if the drop in pressure did not exceed the threshold for at least the minimum duration.

In another embodiment, the monitored hemodynamic parameter is the change in right ventricular pressure versus time (dRVP/dt). In one example of this embodiment, the threshold is expressed as a percent change (20% for example), and the minimum duration after onset of atrial fibrillation is 12 hours. If the patient's dRVP/dt drops from a baseline 400 mmHg/s during normal sinus rhythm to 300 mmHg/s during atrial fibrillation and persists for the minimum time duration, therapy will be enabled because the change (100 mmHg/s) is greater than 20%. Conversely, if the patient's dRVP/dt does not drop below the threshold value, or the decrease in dRVP/dt does not last for at least the minimum duration, therapy will be withheld.

In another embodiment, the monitored hemodynamic performance parameter is thoracic impedance. In one example of this embodiment, the threshold is 4 ohms, and the time duration is 12 hours after onset of atrial fibrillation. If the baseline impedance during normal sinus rhythm is 50 ohms, and the impedance 12 hours after onset of atrial fibrillation is 47 ohms, the change in thoracic impedance is 3 ohms. Since this does not exceed the threshold value of 4 ohms, therapy would be withheld in this particular example.

A variety of hemodynamic parameters may be employed alone or in combination to determine presence of hemodynamic compromise. The various thresholds and durations described above are merely exemplary and should not be taken as limiting.

Figure 3:
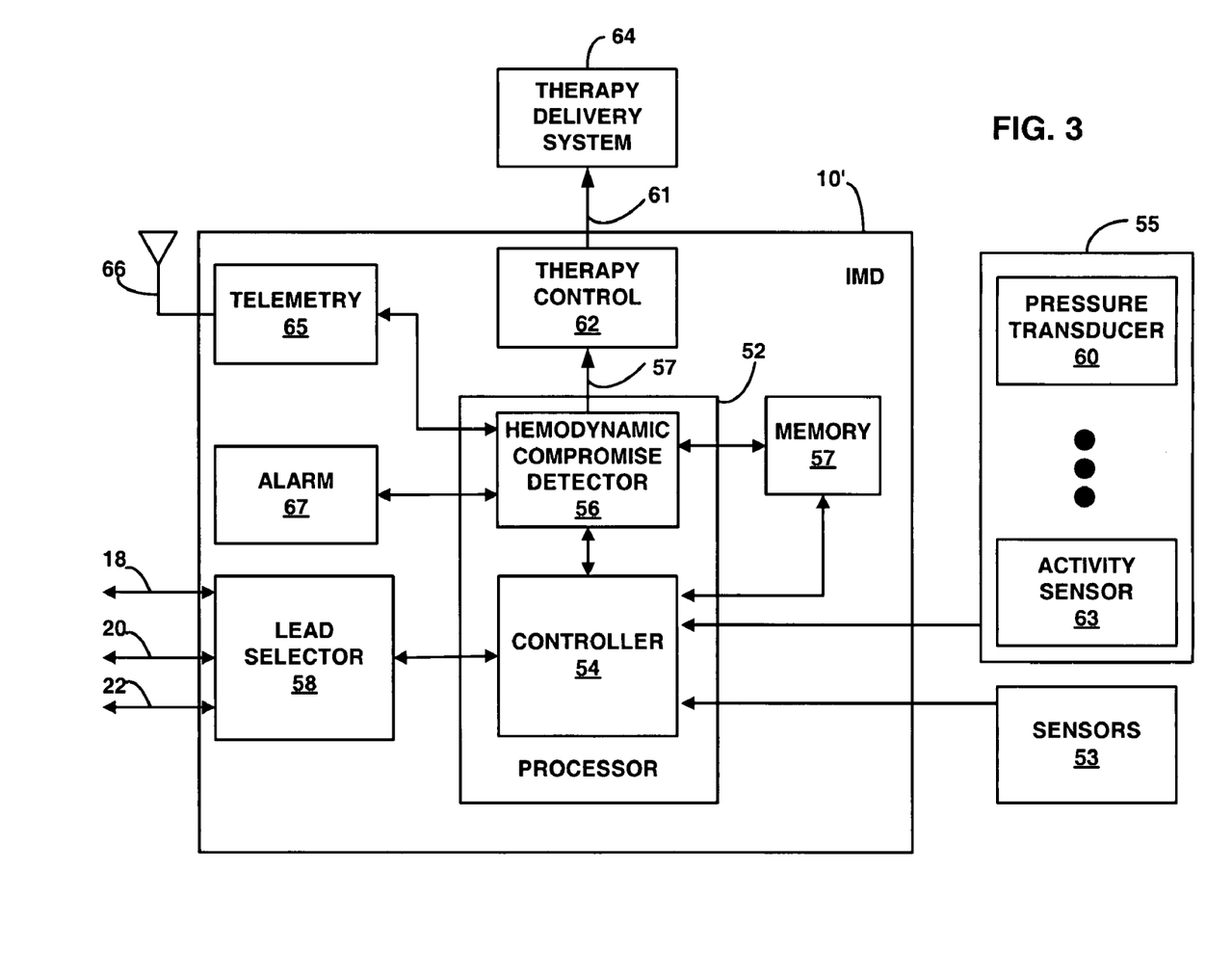
FIG. 3 is a functional block diagram illustrating another embodiment of the IMD shown in FIG. 1.

FIG. 3 is a block diagram illustrating an IMD 10' configured to control atrial defibrillation therapy based on hemodynamic performance of the heart. IMD 10' corresponds substantially to IMD 10 and further includes a therapy control circuit 62 that drives a therapy delivery system 64, and a telemetry circuitry 65 that drives an antenna 66. IMD 10' also includes mechanical transducers 55, including pressure transducer 60 and activity sensor 63, and also may include other sensors 53 external to IMD 10' as needed to supply the appropriate hemodynamic performance information. IMD 10' uses signals received from leads 18, 20 and 22, mechanical transducers 55 or other external sensors 53, depending upon which hemodynamic performance parameters are to be used, to measure hemodynamic performance.

When hemodynamic compromise detector 56 detects a change in the hemodynamic performance that exceeds the pertinent threshold, it transmits a hemodynamic compromise signal to therapy control circuitry 62. For example, processor 52 may generate a hemodynamic compromise signal 61 that causes therapy control circuit 62 to request delivery of therapy from therapy delivery system 64. Therapy delivery system 64 may take, for example, the form of a drug delivery system or electrical stimulation system such as a cardiac pacing or defibrillation circuit.

A memory 57 is provided for storage of digital samples produced by controller 54 and intermediate data stored and retrieved by processor 52. For example, controller 54 may include a number of buffers that hold digital samples for storage in memory. Although not illustrated in FIG. 3 for simplicity, processor 52, memory 57, controller 54 and hemodynamic compromise detector 56 may communicate via a common data and instruction bus, as is well known in the art. The digital samples may be parameterized, in controller 56 or hemodynamic compromise detector 56, to produce values for comparison to a predetermined threshold. Again, the comparison may take place within discrete circuitry provided by hemodynamic compromise detector 56 or via code executed by processor 52. The code may include instructions carried by a computer-readable medium accessible by processor 52, such as memory 57 or other fixed or removable media devices associated with an external programmer/output device communicatively coupled to the processor via telemetry device 65.

Therapy delivery system 64 may take the form of a drug delivery system or electrical stimulation system such as a neurostimulation, pacing, cardioversion or defibrillation circuit. For example, in some embodiments, therapy control circuitry 62 may interact with an electrical stimulation therapy device integrated with IMD 10' to deliver pacing, post-extrasystolic potentiation, cardioversion, defibrillation therapy, and/or communicate with a drug delivery device that may be implanted or external to deliver drug therapy to the patient. In addition, telemetry circuitry 65 alerts an external monitoring system by wireless communication via antenna 66. IMD 10' also may include internal alarm circuitry 67 that is responsive to the hemodynamic compromise signal produced by hemodynamic compromise detection circuitry 56.

Processor 52 indicates the type of arrhythmia detected and the severity of the hemodynamic compromise to therapy control circuit 64 via hemodynamic compromise signal 57. Accordingly, therapy control circuit 62 controls therapy delivery system 64 based on the indications provided by processor 52. For example, therapy control circuit selects the type of therapy, e.g., drug delivery and/or electrical stimulation, the dosage, amplitude, and duration of the therapy, as well as the location for the delivery of the therapy, all based upon the indications provided by processor 52.

Telemetry circuitry 65, as discussed above, communicates an indication of the existence of hemodynamic compromise to an external device via antenna 66. Thus, the indication may be a wireless, radio frequency message that indicates a hemodynamic compromise condition and, in some embodiments, the severity of the hemodynamic compromise. In addition, IMD 10' itself may have an audible alarm within alarm circuitry 67 that notifies the patient when an episode of hemodynamic compromise is occurring. The external device that receives the wireless message may be a programmer/output device that advises a physician or other attendant of the hemodynamic compromise condition, e.g., via a display or a visible or audible alarm. Also, the type and severity of the arrhythmia or other underlying condition and the corresponding hemodynamic performance data may be stored in memory in the external device, or within the IMD 10', for review by a physician.

The components of IMD 10', with the exception of leads 18, 20 and 22, may be housed in a common housing such as that shown in FIG. 1. Alternatively, portions of IMD 10' may be housed separately. For example, therapy delivery system 64 could be integrated with IMD 10' or provided in a separate housing, particularly where the therapy delivery system includes drug delivery capabilities. In this case, therapy control circuit 62 may interact with therapy delivery system 64 via an electrical cable or wireless link.

Figure 4:
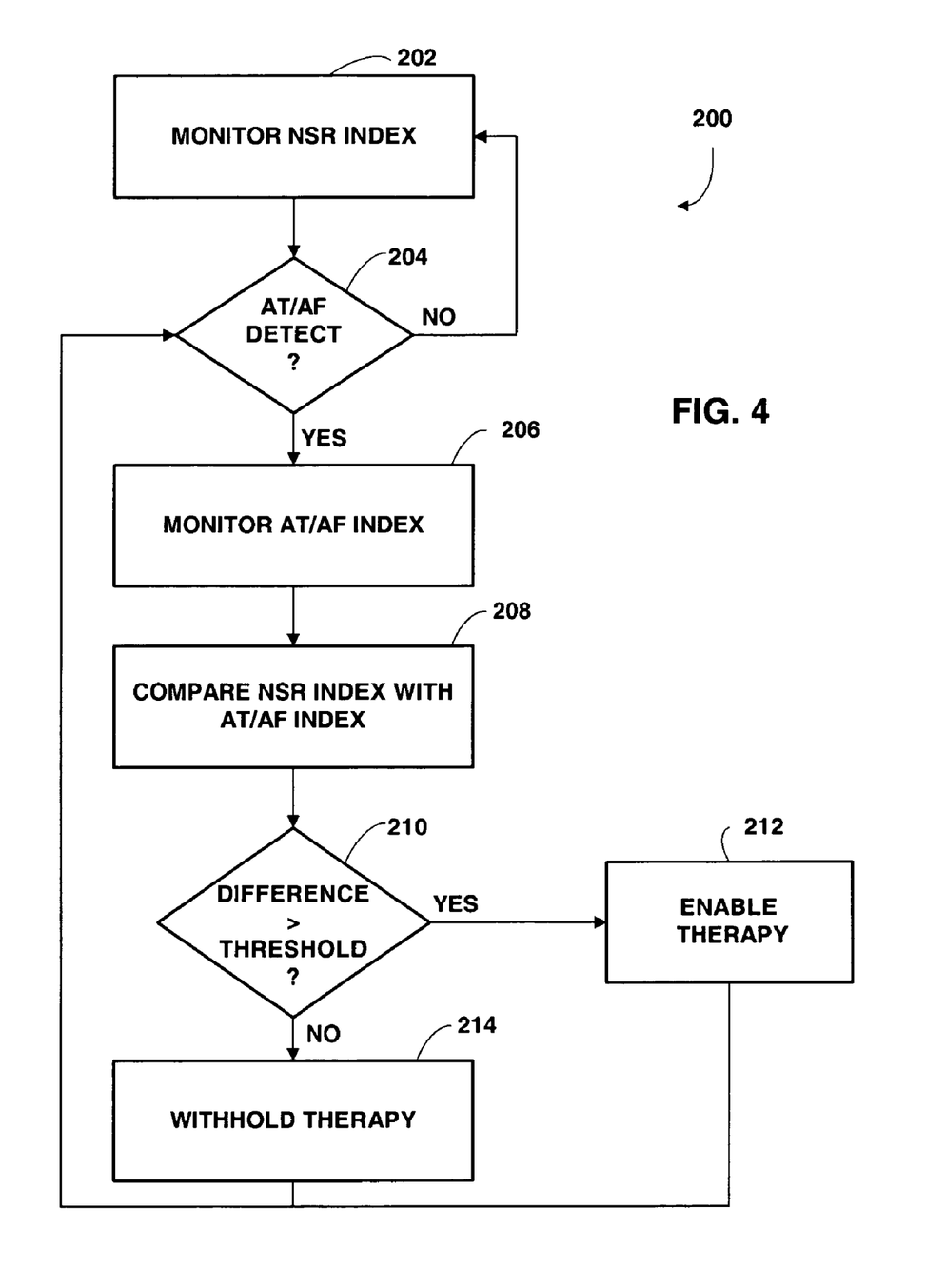
FIG. 4 is a flowchart illustrating a process for controlling application of therapy using hemodynamic sensor feedback.

FIG. 4 is a flowchart illustrating a process for controlling delivery of therapy using hemodynamic sensor feedback. In general, the process (200) first involves monitoring the hemodynamic index of a patient during normal sinus rhythm (NSR) (202). In this way, a baseline hemodynamic index (the NSR index) for the particular patient is established. This value may be periodically updated as necessary to maintain an accurate representation of the patient's baseline hemodynamic index. The NSR index is later used as a basis for comparison during presence of an atrial arrhythmia to determine whether a change in hemodynamic performance of the heart exceeds a threshold, and thus to determine whether atrial defibrillation therapy should be applied.

The heart is also continuously monitored to detect abnormal heart rhythms such as atrial tachycardia (AT) or atrial fibrillation (AF) events (204). When an AT or AF event is detected, the hemodynamic index of the patient is measured during the AT or AF event to obtain an AT/AF index (206). The AT/AF index is next compared with the NSR index (208). The difference is then compared to a threshold value (210). The threshold value is indicative of a specified minimum change in hemodynamic performance of the heart. Hemodynamic compromise is present when this threshold change is detected. The threshold change, and thus a minimum level of hemodynamic compromise, must be present before therapy is applied. If the difference or change does not exceed the threshold (210), therapy is withheld (214). If, on the other hand, the change in hemodynamic performance does exceed the threshold, therapy is enabled (212).

Figure 5:
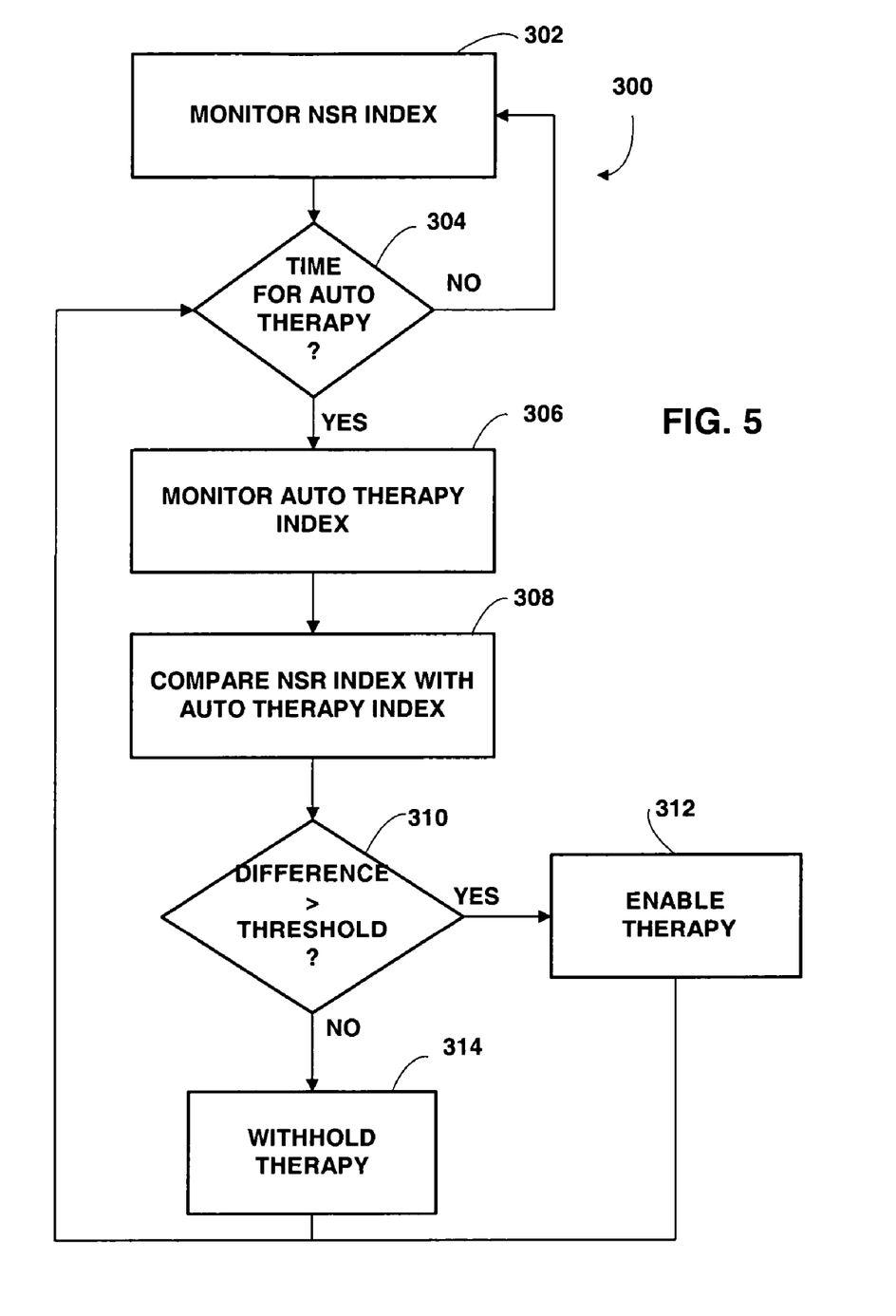
FIG. 5 is a flowchart illustrating another process for controlling application of therapy using hemodynamic sensor feedback.

FIG. 5 shows another embodiment of a process using the hemodynamic sensor feedback. This embodiment is relevant to those systems in which an IMD is programmed to apply atrial defibrillation therapy at preprogrammed times of the day, for example, every night at 3 AM. Operation of this embodiment is similar to that described above with respect to FIG. 4. Again, the process (300) involves monitoring the hemodynamic index of a patient during normal sinus rhythm (NSR) (302). In this way, the baseline hemodynamic index (the NSR index) for the particular patient is established.

At the programmed time for automatic delivery of atrial defibrillation therapy (304), the hemodynamic index of the patient is measured to determine an auto therapy index (306). The auto therapy index is next compared with the NSR index (308). The difference is then compared to the pertinent threshold (310). Once again, the threshold is indicative of a minimum change in hemodynamic performance of the heart. If the difference does not exceed the threshold (310), defibrillation therapy is withheld (314). If, on the other hand, the change in hemodynamic performance does exceed the threshold, therapy is enabled (312).

The system can be programmed to allow for early application of therapy in the event that the change in hemodynamic performance exceeds the threshold (310). If the system is so programmed, early delivery of atrial defibrillation therapy, such as delivery initiated by the patient, is allowed (312).

One or more of the techniques described herein may be partially or wholly executed in software. For example, a computer-readable medium may store or otherwise comprise computer-readable instructions, i.e., program code that can be executed by a processor to carry out one of more of the techniques described above. For example, the computer readable medium may comprise random access memory (RAM), read-only memory (ROM), non-volatile random access memory (NVRAM), electrically erasable programmable read-only memory (EEPROM), flash memory, magnetic or optical media, or the like.

Various embodiments of the invention have been described. These and other embodiments are within the scope of the following claims.

The invention claimed is:

1. A method comprising:
   detecting atrial fibrillation;
   measuring hemodynamic performance during atrial fibrillation; and
   enabling therapy based on the measured hemodynamic performance;
   wherein enabling therapy comprises determining whether hemodynamic compromise is present based on the hemodynamic performance during fibrillation, enabling the therapy when hemodynamic compromise is present, and disabling therapy when hemodynamic compromise is not present.

2. The method of claim 1, further comprising delivering the therapy when the therapy is enabled.

3. The method of claim 1, wherein the therapy includes at least one of drug delivery, electrical stimulation, modification of ongoing electrical stimulation, and a combination of drug delivery and electrical stimulation.

4. The method of claim 3, wherein the therapy is atrial defibrillation therapy.

5. The method of claim 1, further comprising storing information about the hemodynamic compromise.

6. The method of claim 1, wherein determining whether hemodynamic compromise is present further comprises:
   measuring a hemodynamic performance baseline during normal sinus rhythm;
   comparing the hemodynamic performance during fibrillation to the hemodynamic performance baseline to determine whether a change in hemodynamic performance has occurred; and
   determining presence of hemodynamic compromise when the change exceeds a threshold.

7. The method of claim 6, wherein the hemodynamic performance baseline and the hemodynamic performance during fibrillation are measured using at least one hemodynamic performance parameter.

8. The method of claim 7, wherein the hemodynamic performance parameter includes at least one of electrogram (EGM), electrocardiogram (ECG), atrial pressure, ventricular pressure, arterial pressure, flow, pulmonary venous flow, acceleration, atrial dimension, ventricular dimension, thoracic impedance, intramyocardial impedance, velocity, QT interval, ST segment, blood oxygen content, myocardial oxygen consumption, change in right ventricular pressure versus time (dRVP/dt), and MVO2/PO2.

9. The method of claim 7, wherein the hemodynamic performance baseline and the hemodynamic performance during fibrillation are each measured using a combination of at least two hemodynamic performance parameters.

10. The method of claim 6, wherein the threshold represents a specified minimum change in the hemodynamic performance during fibrillation compared to the hemodynamic performance baseline.

11. The method of claim 10, wherein the threshold is expressed as an absolute change in hemodynamic performance.

12. The method of claim 10, wherein the threshold is expressed as a percentage change in hemodynamic performance.

13. The method of claim 10, wherein the threshold is expressed as a rate of change in hemodynamic performance.

14. The method of claim 6, further comprising quantifying severity of hemodynamic compromise based on the measured hemodynamic performance during fibrillation.

15. A system for controlling application of therapy to a heart, the system comprising:
    a first sensor that detects atrial fibrillation;
    a second sensor that measures hemodynamic performance during fibrillation; and
    a processor that is programmed whether hemodynamic compromise is present based on the hemodynamic performance during atrial fibrillation, and enables delivery of therapy when hemodynamic compromise is present and disables delivery of therapy when hemodynamic compromise is not present.

16. The system of claim 15, wherein the processor stores information about the hemodynamic compromise.

17. The system of claim 15, wherein the therapy includes at least one of drug delivery, electrical stimulation, modification of ongoing electrical stimulation, and a combination of drug delivery and electrical stimulation.

18. The system of claim 17, wherein the therapy is atrial defibrillation therapy.

19. The system of claim 15, wherein the second sensor further measures hemodynamic performance during normal sinus rhythm.

20. The system of claim 19, wherein the processor compares the hemodynamic performance during fibrillation to the hemodynamic performance during normal sinus rhythm to determine whether a change in hemodynamic performance has occurred, and to determine presence of hemodynamic compromise when the change exceeds a threshold.

21. The system of claim 20, wherein the hemodynamic performance during normal sinus rhythm and the hemodynamic performance during fibrillation are measured using at least one hemodynamic performance parameter.

22. The system of claim 21, wherein the hemodynamic performance parameter includes at least one of electrogram (EGM), electrocardiogram (ECG), atrial pressure, ventricular pressure, arterial pressure, flow, pulmonary venous flow, acceleration, atrial dimension, ventricular dimension, thoracic impedance, intramyocardial impedance, velocity, QT interval, ST segment, blood oxygen content, myocardial oxygen consumption, change in right ventricular pressure versus time (dRVP/dt), and MVO2/PO2.

23. The system of claim 20, wherein the hemodynamic performance during normal sinus rhythm and the hemodynamic performance during fibrillation are measured using a combination of at least two hemodynamic performance parameters.

24. The system of claim 15, wherein the threshold represents a specified minimum change in the hemodynamic performance during fibrillation compared to the hemodynamic performance during normal sinus rhythm.

25. The system of claim 24, wherein the processor quantifies severity of hemodynamic compromise based on the measured hemodynamic performance.

26. The system of claim 15, further including a telemetry device for wireless transmission of a message when hemodynamic compromise is present.

27. The system of claim 15, further including a telemetry device for wireless transmission of a message upon delivery of therapy.

28. A system for controlling application of therapy to a heart, the system comprising:
   means for detecting atrial fibrillation;
   means for measuring hemodynamic performance during atrial fibrillation;
   means for determining whether hemodynamic compromise is present based on the measured hemodynamic performance;
   means for enabling delivery of therapy when hemodynamic compromise is present; and
   means for disabling delivery of therapy when hemodynamic compromise is not present.

29. The system of claim 28, wherein the therapy is atrial defibrillation therapy.

30. The system of claim 28, wherein the therapy includes at least one of drug delivery, electrical stimulation, and a combination of drug delivery and electrical stimulation.

31. The system of claim 28, wherein the hemodynamic performance is measured using at least one of electrogram (EGM), electrocardiogram (ECG), atrial pressure, ventricular pressure, arterial pressure, flow, pulmonary venous flow, acceleration, atrial dimension, ventricular dimension, thoracic impedance, intramyocardial impedance, velocity, QT interval, ST segment, blood oxygen content, myocardial oxygen consumption, change in right ventricular pressure versus time (dRVP/dt), and MVO2/PO2.

32. A method of controlling application of therapy, the method comprising:
   detecting atria fibrillation
   programming a time period to automatically deliver the therapy;
   measuring hemodynamic performance at the programmed time period;
   determining whether hemodynamic compromise is present at the programmed time period based on the measured hemodynamic performance; and
   enabling delivery of therapy when hemodynamic compromise is present; and
   disabling delivery of therapy when hemodynamic compromise is not present.

33. The method of claim 32, wherein determining whether hemodynamic compromise is present includes detecting a specified minimum change in hemodynamic performance measured at the programmed time period compared to hemodynamic performance measured during normal sinus rhythm.

34. The method of claim 32, wherein the therapy is atrial defibrillation therapy.

35. The method of claim 34, wherein the therapy includes at least one of drug delivery, electrical stimulation, modification of ongoing electrical stimulation, and a combination of drug delivery and electrical stimulation.

36. A computer-readable medium containing instructions for causing a processor to:
   detect atrial fibrillation;
   measure hemodynamic performance detect atrial fibrillation;
   measure hemodynamic performance during normal sinus rhythm;
   compare the hemodynamic performance during fibrillation to the hemodynamic performance during normal sinus rhythm to determine whether a change in hemodynamic performance has occurred;
   detecting presence of hemodynamic compromise when the change exceeds a threshold;
   enable delivery of therapy when hemodynamic compromise is present; and
   disable delivery of therapy when hemodynamic compromise is not present.

37. A method comprising:
   detecting atrial fibrillation;
   measuring hemodynamic performance during atrial fibrillation; and
   enabling therapy based on the measured hemodynamic performance;
   wherein enabling therapy comprises determining whether hemodynamic compromise is present based on the hemodynamic performance during fibrillation, enabling the therapy when hemodynamic compromise is present, and disabling therapy when hemodynamic compromise is not present, and
   wherein determining whether hemodynamic compromise is present further comprises:
   measuring a hemodynamic performance baseline during normal sinus rhythm;
   comparing the hemodynamic performance during fibrillation to the hemodynamic performance baseline to determine whether a change in hemodynamic performance has occurred; and
   determining presence of hemodynamic compromise when the change exceeds a threshold for at least a predetermined minimum time period.

* * * * *

UNITED STATES PATENT AND TRADEMARK OFFICE
CERTIFICATE OF CORRECTION

PATENT NO. : 7,336,994 B2
APPLICATION NO. : 10/760155
DATED : February 26, 2008
INVENTOR(S) : Hettrick et al.

It is certified that error appears in the above-identified patent and that said Letters Patent is hereby corrected as shown below:

Column 11
Line 32, delete "atria" and insert in place thereof --atrial--

Signed and Sealed this

Eleventh Day of August, 2009

David J. Kappos
*Director of the United States Patent and Trademark Office*